(12) United States Patent
Coleman et al.

(10) Patent No.: US 7,723,502 B2
(45) Date of Patent: May 25, 2010

(54) **MODIFIED *LUCIOLA CRUCIATA* LUCIFERASE GENE AND PROTEIN**

(75) Inventors: Daniel J. Coleman, Corvallis, OR (US); John J. Naleway, Eugene, OR (US); Gabriele M. Cook, Eugene, OR (US)

(73) Assignee: Marker Gene Technologies, Inc, Eugene, OR (US)

( * ) Notice: Subject to any disclaimer, the term of this patent is extended or adjusted under 35 U.S.C. 154(b) by 0 days.

(21) Appl. No.: 12/287,561

(22) Filed: Oct. 10, 2008

(65) Prior Publication Data

US 2010/0093029 A1  Apr. 15, 2010

(51) Int. Cl.
*C07H 21/02* (2006.01)
*C07H 21/04* (2006.01)
*C12P 21/06* (2006.01)
*C12P 21/04* (2006.01)
*C12N 15/00* (2006.01)

(52) U.S. Cl. .................... 536/23.1; 536/23.2; 435/69.1; 435/69.7; 435/71.1; 435/71.2; 435/320.1

(58) Field of Classification Search ........................ None
See application file for complete search history.

(56) References Cited

OTHER PUBLICATIONS

Branden et al., "Introduction to Protein Structure Second Edition", Garland Publishing Inc., New York, 1999.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
Masuda et al. (Cloning and sequence analysis of cDNA for luciferase of a Japanese firefly, *Luciola cruciata*, Gene, 77: 265-270, 1989).*

* cited by examiner

*Primary Examiner*—Suzanne M. Noakes
*Assistant Examiner*—Jae W Lee
(74) *Attorney, Agent, or Firm*—Timothy L. McCutcheon

(57) ABSTRACT

A codon optimized and stabilized luciferase gene based upon the sequence of the natural luciferase gene isolated from *Luciola cruciata* (Japanese firefly) and a novel recombinant DNA characterized by incorporating this new gene coding for a novel luciferase into a vector DNA for improved activities in mammalian cells, are disclosed. This new luciferase exhibits long-wavelength light emission, as well as improved thermostability and higher expression levels in mammalian cell systems, compared to native luciferase.

7 Claims, 5 Drawing Sheets

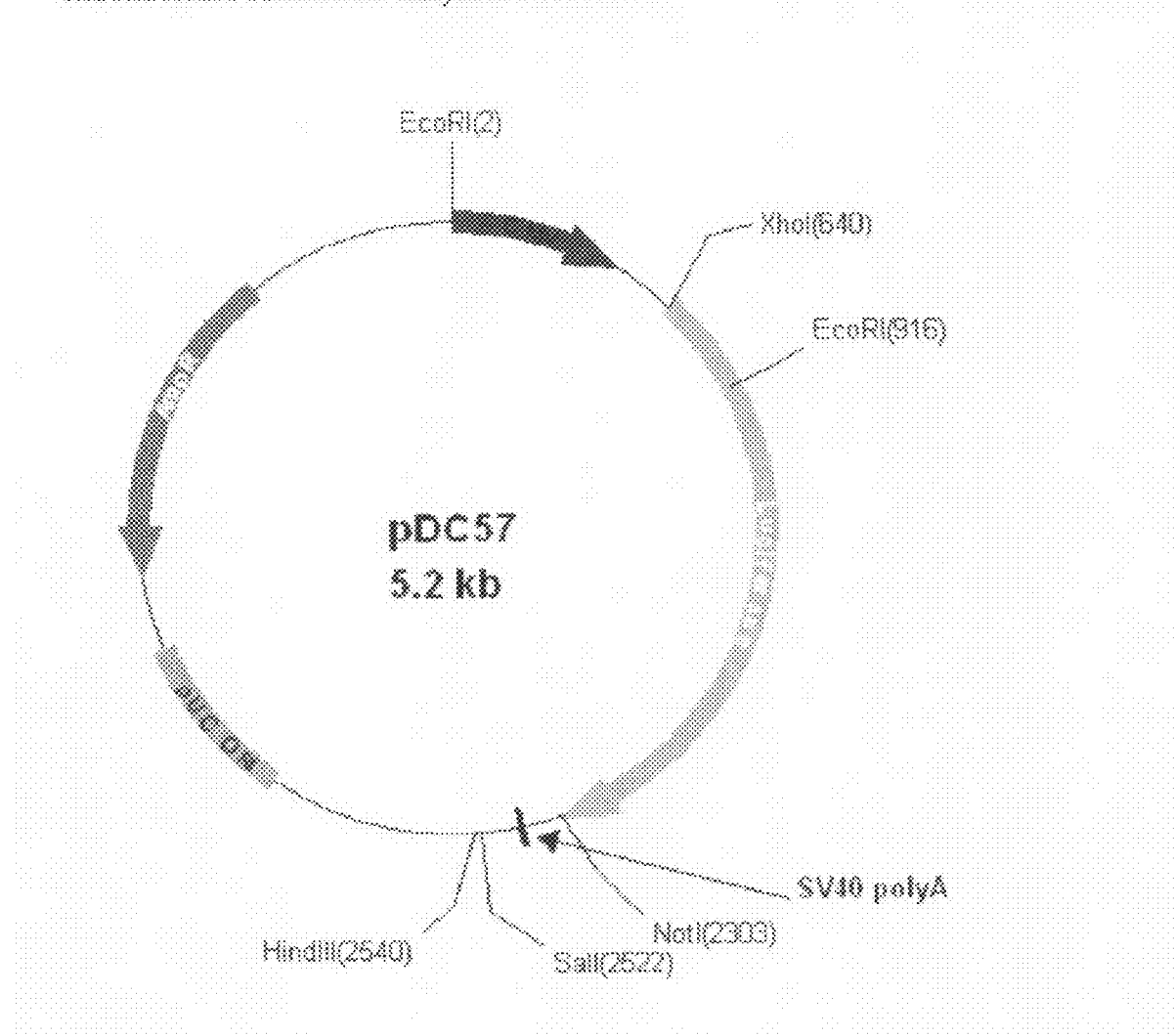
Figure 1. Cleavage map of recombinant plasmid pDC57 DNA with elements and endonuclease restriction enzymes sites listed.

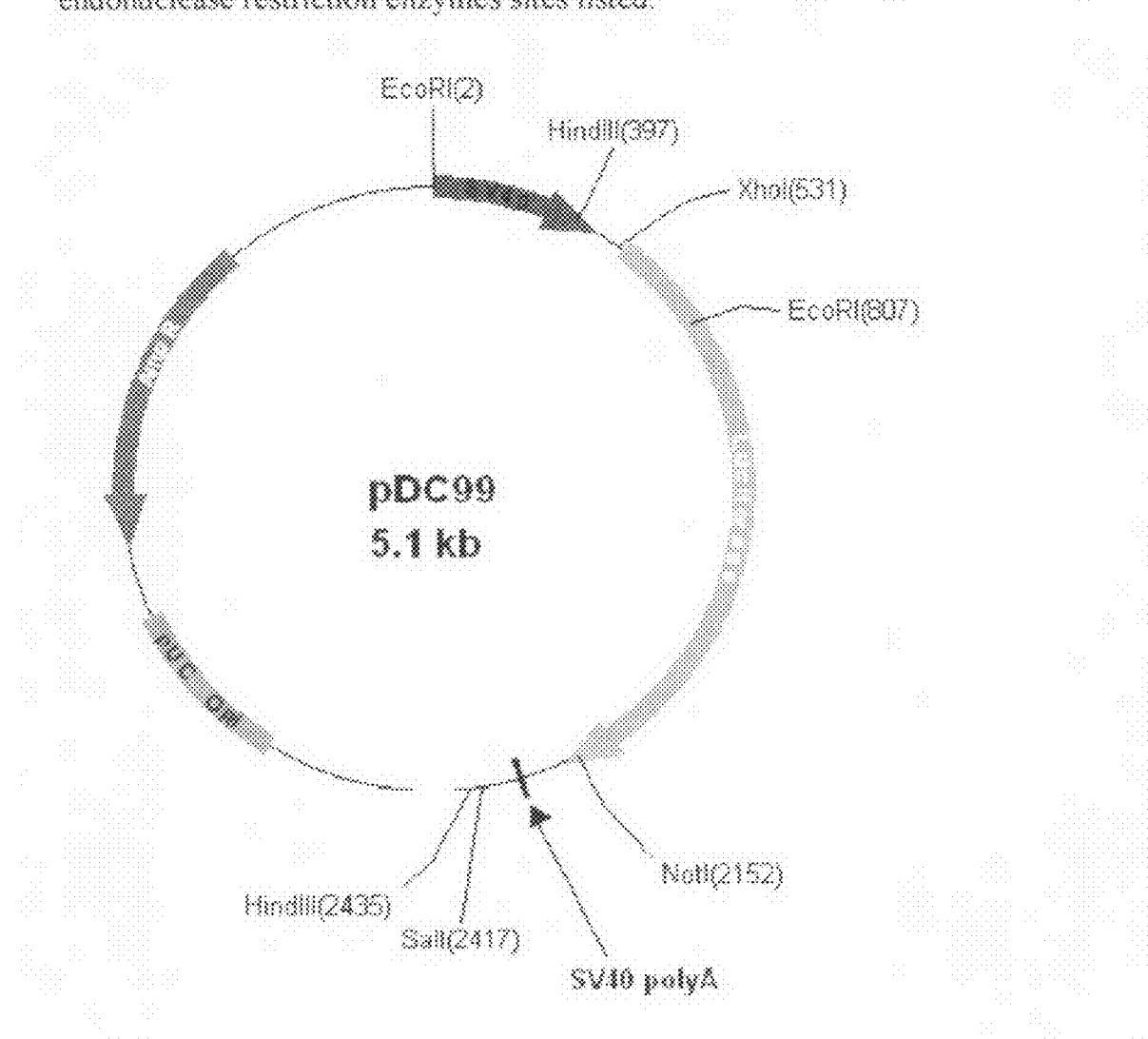
Figure 2. Cleavage map of recombinant plasmid pDC99 DNA with elements and endonuclease restriction enzymes sites listed.

Figure 3. Comparison of native *L. cruciata* luciferase sequence with codon optimized nucleotide sequence of the present invention. The sequence below shows the optimized sequence, SEQ ID NO:3 with changes from native sequence in bold/underline.

```
   1 ATGGAAAATATGGAAAACGACGAGAACATCGTGGTGGGCCCCAAGCCCTT
  51 CTACCCCATCGAGGAAGGCAGCGCCGGCACCCAGCTGCGGAAGTACATGG
 101 AAAGATACGCCAAGCTGGGCGCCATTGCCTTCACCAACGCCGTGACCGGC
 151 GTGGACTACAGCTACGCCGAGTACCTGGAAAAGAGCTGCTGCCTGGGCAA
 201 GGCTCTGCAGAACTACGGCCTGGTGGTGGACGGCCGGATCGCCCTGTGCA
 251 GCGAGAACTGCGAGGAATTCTTCATCCCCGTGATCGCCGGCCTGTTCATC
 301 GGCGTGGGCGTGGCTCCCACCAACGAGATCTACACCCTGCGGGAGCTGGT
 351 GCACAGCCTGGGCATCAGCAAGCCCACCATCGTGTTCAGCAGCAAGAAGG
 401 GCCTGGACAAAGTCATCACCGTGCAGAAACCGTGACCACCATCAAGACC
 451 ATCGTGATCCTGGACAGCAAGGTGGACTACCGGGGCTACCAGTGCCTGGA
 501 CACCTTCATCAAGCGGAACACCCCCCCTGGCTTCCAGGCCAGCAGCTTCA
 551 AGACCGTGGAGGTGGACCGGAAAGAACAGGTGGCCCTGATCATGAACAGC
 601 AGCGGCAGCACCGGCCTGCCCAAGGGCGTGCAGCTGACCCACGAGAACAC
 651 CGTGACCCGGTTCAGCCACGCCAGGGACCCCATCTACGGCAACCAGGTGT
 701 CCCCCGGCACCGCCGTGCTGACCGTGGTGCCCTTCCACCACGGCTTCGGC
 751 ATGTTCACCACCCTGGGCTACCTGATCTGCGGCTTCCGGGTGGTGATGCT
 801 GACCAAGTTCGACGAGGAAACCTTCCTGAAAACCCTGCAGGACTACAAGT
 851 GCACCTACGTGATTCTGGTGCCCACCCTGTTCGCCATCCTGAACAAGAGC
 901 GAGCTGCTGAACAAGTACGACCTGAGCAACCTGGTGGAGATCGCCAGCGG
 951 CGGAGCCCCCCTGAGCAAAGAAGTGGGAGAGGCCGTCGCCAGGCGGTTCA
1001 ATCTGCCCGGCGTGCGGCAGGGCTACGGCCTGACCGAGACAACCAGCGCC
1051 ATCATCATCACCCCGAGGGCGACGACAAGCCTGGAGCCAGCGGCAAGGT
1101 GGTGCCCCTGTTCAAGGCCAAAGTGATCGACCTGGACACCAAGAAGAGCC
1151 TGGGCCCCAACAGACGGGGCGAAGTGTGCGTGAAGGGCCCCATGCTGATG
1201 AAGGGCTACGTGAACAACCCCGAGGCCACCAAAGAGCTGATCGACGAAGA
1251 GGGCTGGCTGCACACCGGCGACATCGGCTACTACGACGAAGAGAAGCACT
1301 TCTTCATCGTGGACCGGCTGAAGAGCCTGATCAAGTACAAGGGCTATCAG
1351 GTGCCCCTGCCGAGCTGGAAAGCGTCCTGCTGCAGCACCCCAGCATCTT
1401 CGACGCCGGCGTGGCCGGGGTGCCAGATCCTGTGGCCGGCGAGCTGCCTG
1451 GCGCCGTGGTGGTGCTGGAATCCGGCAAGAACATGACCGAGAAAGAAGTG
1501 ATGGACTACGTCGCCAGCCAGGTGTCCAACGCCAAGCGGCTGAGAGGCGG
1551 CGTGAGATTCGTGGACGAAGTGCCAAAGGGCCTGACCGGCAAGATCGACG
1601 GCAGGGCCATCCGGGAGATCCTGAAGAAACCCGTGGCCAAGATG
```

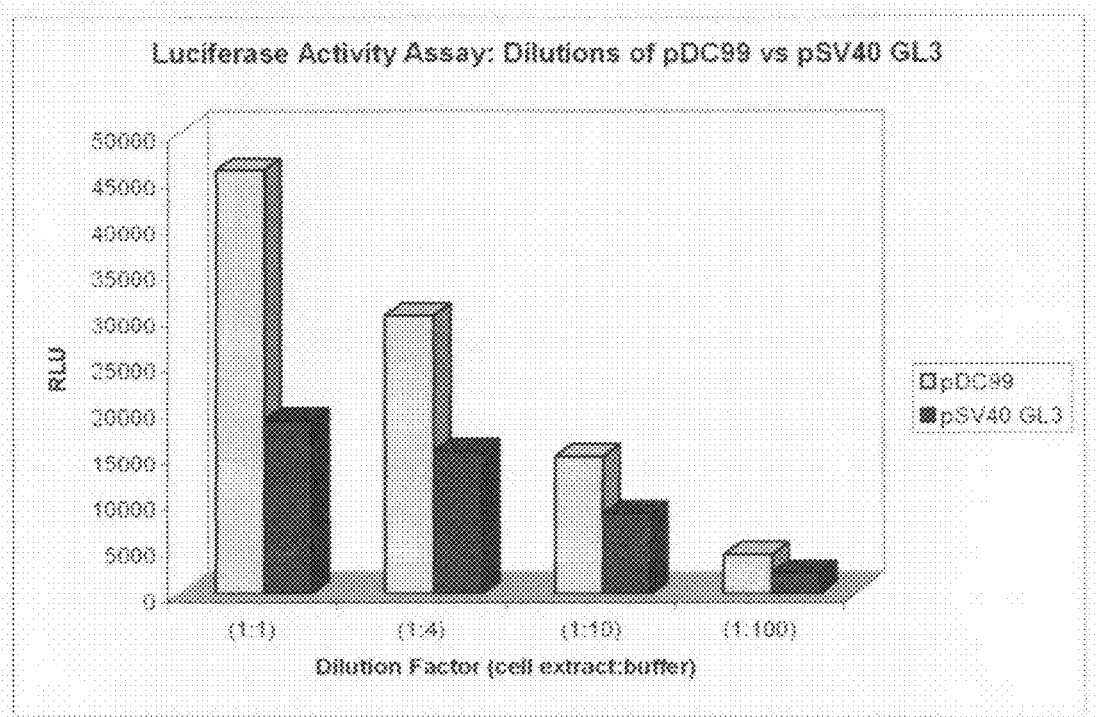
Figure 4. Analysis of Luciferase Expression Levels using the pDC99 Vector and Comparison to the Luciferase Expression Using the *Photinus pyralis* luciferase Vector pSV40-GL3 in mammalian cells.

Figure 5. Analysis of the thermal stability of the modified *Luciola cruciata* luciferase protein versus the *Photinus pyralis* wild type protein (a) at 25°C and (b) at 37°C.
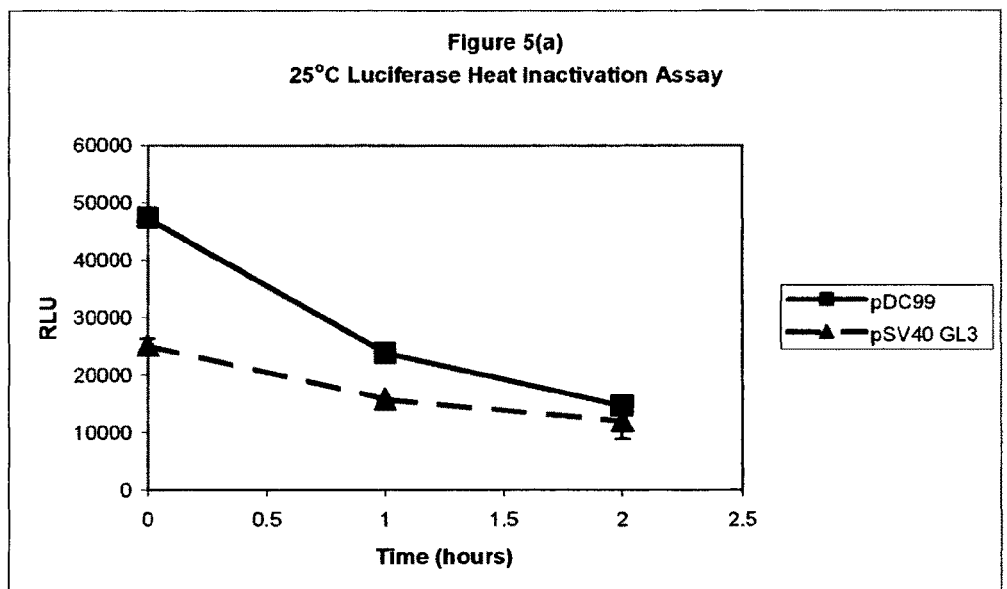
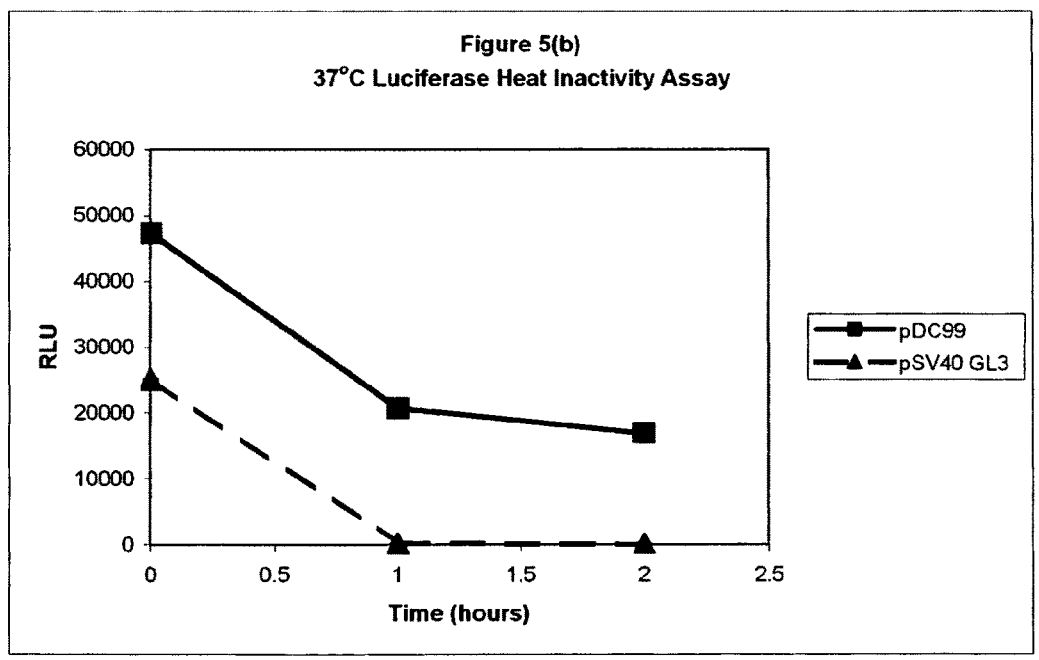

SEQUENCE LISTING

<160> NUMBER OF SEQ ID NOS: 24

<210> SEQ ID NO 1
<211> LENGTH: 1644
<212> TYPE: DNA
<213> ORGANISM: Luciola cruciata

<400> SEQUENCE: 1

```
atggaaaaca tggaaaacga tgaaaatatt gtagttggac ctaaaccgtt ttaccctatc      60
gaagagggat ctgctggaac acaattacgc aaatacatgg agcgatatgc aaaacttggc     120
gcaattgctt ttacaaatgc agttactggt gttgattatt cttacgccga atacttggag     180
aaatcatgtt gtctaggaaa agctttgcaa aattatggtt tggttgttga tggcagaatt     240
gcgttatgca gtgaaaactg tgaagaattt tttattcctg taatagccgg actgtttata     300
ggtgtaggtg ttgcacccac taatgagatt tacactttac gtgaactggt tcacagttta     360
ggtatctcta aaccaacaat tgtatttagt tctaaaaaag cttagataa agttataaca     420 gtacagaaaa cagtaactac tattaaaacc attgttatac tagatagcaa agttgattat     480
cgaggatatc aatgtctgga caccttata aaagaaaca ctccaccagg ttttcaagca     540
tccagtttca aaactgtgga agttgaccgt aaagaacaag ttgctcttat aatgaactct     600
tcgggttcta ccggtttgcc aaaaggcgta caacttactc acgaaaatac agtcactaga     660
ttttctcatg ctagagatcc gatttatggt aaccaagttt caccaggcac cgctgtttta     720
actgtcgttc cattccatca tggttttggt atgttcacta ctctagggta tttaatttgt     780
ggttttcgtg ttgtaatgtt aacaaaattc gatgaagaaa catttttaaa aactctacaa     840
gattataaat gtacaagtgt tattcttgta ccgaccttgt ttgcaattct caacaaaagt     900
gaattactca ataaatacga tttgtcaaat ttagttgaga ttgcatctgg cggagcacct     960
ttatcaaaag aagttggtga agctgttgct agacgcttta atcttcccgg tgttcgtcaa    1020
ggttatggtt taacagaaac aacatctgcc attattatta caccagaagg agacgataaa    1080
ccaggagctt ctggaaaagt cgtgccgttg tttaaagcaa aagttattga tcttgatacc    1140
aaaaaatctt taggtcctaa cagacgtgga gaagtttgtg ttaaaggacc tatgcttatg    1200
aaaggttatg taaataatcc agaagcaaca aaagaactta ttgacgaaga aggttggctg    1260
cacaccggag atattggata ttatgatgaa gaaaaacatt tctttattgt cgatcgtttg    1320
aagtctttaa tcaaatacaa aggataccaa gtaccacctg ccgaattaga atccgttctt    1380
ttgcaacatc catctatctt tgatgctggt gttgccggcg ttcctgatcc tgtagctggc    1440
gagcttccag gagccgttgt tgtactggaa agcggaaaaa atatgaccga aaaagaagta    1500
atggattatg ttgcaagtca agtttcaaat gcaaacgtt tacgtggtgg tgttcgtttt    1560
gtggatgaag tacctaaagg tcttactgga aaaattgacg gcagagcaat tagagaaatc    1620
cttaagaaac cagttgctaa gatg                                          1644
```

<210> SEQ ID NO 2
<211> LENGTH: 548
<212> TYPE: PRT
<213> ORGANISM: Luciola cruciata

<400> SEQUENCE: 2

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
        35                  40                  45

Thr Gly Val Asp Tyr Ser Tyr Ala Glu Tyr Leu Glu Lys Ser Cys Cys
    50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Thr Val Thr Arg Phe Ser His Ala
    210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
                245                 250                 255

Tyr Leu Ile Cys Gly Phe Arg Val Val Met Leu Thr Lys Phe Asp Glu
            260                 265                 270

Glu Thr Phe Leu Lys Thr Leu Gln Asp Tyr Lys Cys Thr Ser Val Ile
        275                 280                 285

Leu Val Pro Thr Leu Phe Ala Ile Leu Asn Lys Ser Glu Leu Leu Asn
    290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
                325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Ser Leu
    370                 375                 380

```
Gly Pro Asn Arg Arg Gly Glu Val Cys Val Lys Gly Pro Met Leu Met
385                 390                 395                 400

Lys Gly Tyr Val Asn Asn Pro Glu Ala Thr Lys Glu Leu Ile Asp Glu
            405                 410                 415

Glu Gly Trp Leu His Thr Gly Asp Ile Gly Tyr Tyr Asp Glu Glu Lys
            420                 425                 430

His Phe Phe Ile Val Asp Arg Leu Lys Ser Leu Ile Lys Tyr Lys Gly
            435                 440                 445

Tyr Gln Val Pro Pro Ala Glu Leu Glu Ser Val Leu Leu Gln His Pro
            450                 455                 460

Ser Ile Phe Asp Ala Gly Val Ala Gly Val Pro Asp Pro Val Ala Gly
465                 470                 475                 480

Glu Leu Pro Gly Ala Val Val Val Leu Glu Ser Gly Lys Asn Met Thr
                485                 490                 495

Glu Lys Glu Val Met Asp Tyr Val Ala Ser Gln Val Ser Asn Ala Lys
                500                 505                 510

Arg Leu Arg Gly Gly Val Arg Phe Val Asp Glu Val Pro Lys Gly Leu
            515                 520                 525

Thr Gly Lys Ile Asp Gly Arg Ala Ile Arg Glu Ile Leu Lys Lys Pro
            530                 535                 540

Val Ala Lys Met
545

<210> SEQ ID NO 3
<211> LENGTH: 1644
<212> TYPE: DNA
<213> ORGANISM: Luciola cruciata

<400> SEQUENCE: 3
atggaaaata tggaaaacga cgagaacatc gtggtgggcc ccaagccctt ctaccccatc      60
gaggaaggca gcgccggcac ccagctgcgg aagtacatgg aaagatacgc caagctgggc    120
gccattgcct tcaccaacgc cgtgaccggc gtggactaca gctacgccga gtacctggaa    180
aagagctgct gcctgggcaa ggctctgcag aactacggcc tggtggtgga cggccggatc    240
gccctgtgca gcgagaactg cgaggaattc ttcatccccg tgatcgccgg cctgttcatc    300
ggcgtgggcg tggctcccac caacgagatc tacaccctgc gggagctggt gcacagcctg    360
ggcatcagca agcccaccat cgtgttcagc agcaagaagg gcctggacaa agtcatcacc    420
gtgcagaaaa ccgtgaccac catcaagacc atcgtgatcc tggacagcaa ggtggactac    480
cggggctacc agtgcctgga caccttcatc aagcggaaca cccccctgg cttccaggcc    540 agcagcttca gaccgtgga ggtggaccgg aaagaacagg tggccctgat catgaacagc    600
agcggcagca ccggcctgcc caagggcgtg cagctgaccc acgagaacac cgtgacccgg    660
ttcagccacg ccagggaccc catctacggc aaccaggtgt cccccggcac cgccgtgctg    720
accgtggtgc ccttccacca cggcttcggc atgttcacca ccctgggcta cctgatctgc    780
ggcttccggg tggtgatgct gaccaagttc gacgaggaaa ccttcctgaa aaccctgcag    840
gactacaagt gcacctacgt gattctggtg cccaccctgt tcgccatcct gaacaagagc    900
gagctgctga acaagtacga cctgagcaac ctggtggaga tcgccagcgg cggagccccc    960
ctgagcaaag aagtgggaga ggccgtcgcc aggcggttca atctgccgg cgtgcggcag   1020 ggctacggcc tgaccgagac aaccagcgcc atcatcatca ccccgagggg cgacgacaag   1080
cctggagcca gcggcaaggt ggtgcccctg ttcaaggcca agtgatcga cctggacacc   1140
```

-continued

```
aagaagagcc tgggccccaa cagacggggc gaagtgtgcg tgaagggccc catgctgatg    1200
aagggctacg tgaacaaccc cgaggccacc aaagagctga tcgacgaaga gggctggctg    1260
cacaccggcg acatcggcta ctacgacgaa gagaagcact tcttcatcgt ggaccggctg    1320
aagagcctga tcaagtacaa gggctatcag gtgcccctg ccgagctgga aagcgtcctg     1380
ctgcagcacc ccagcatctt cgacgccggc gtggccgggg tgccagatcc tgtggccggc    1440
gagctgcctg gcgccgtggt ggtgctggaa tccggcaaga acatgaccga aaagaagtg     1500 atggactacg tcgccagcca ggtgtccaac gccaagcggc tgagaggcgg cgtgagattc    1560
gtggacgaag tgccaaaggg cctgaccggc aagatcgacg cagggccat ccgggagatc     1620 ctgaagaaac ccgtggccaa gatg                                            1644
```

<210> SEQ ID NO 4
<211> LENGTH: 548
<212> TYPE: PRT
<213> ORGANISM: Luciola cruciata

<400> SEQUENCE: 4

```
Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
                20                  25                  30

Met Glu Arg Tyr Ala Lys Leu Gly Ala Ile Ala Phe Thr Asn Ala Val
        35                  40                  45

Thr Gly Val Asp Tyr Ser Tyr Ala Glu Tyr Leu Glu Lys Ser Cys Cys
    50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
                100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
                180                 185                 190

Gln Val Ala Leu Ile Met Asn Ser Ser Gly Ser Thr Gly Leu Pro Lys
        195                 200                 205

Gly Val Gln Leu Thr His Glu Asn Thr Val Thr Arg Phe Ser His Ala
    210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
                245                 250                 255

Tyr Leu Ile Cys Gly Phe Arg Val Val Met Leu Thr Lys Phe Asp Glu
                260                 265                 270

Glu Thr Phe Leu Lys Thr Leu Gln Asp Tyr Lys Cys Thr Tyr Val Ile
        275                 280                 285
```

```
Leu Val Pro Thr Leu Phe Ala Ile Leu Asn Lys Ser Glu Leu Leu Asn
    290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
            325                 330                 335

Gly Val Arg Gln Gly Tyr Gly Leu Thr Glu Thr Thr Ser Ala Ile Ile
        340                 345                 350

Ile Thr Pro Glu Gly Asp Asp Lys Pro Gly Ala Ser Gly Lys Val Val
    355                 360                 365

Pro Leu Phe Lys Ala Lys Val Ile Asp Leu Asp Thr Lys Lys Ser Leu
370                 375                 380

Gly Pro Asn Arg Arg Gly Glu Val Cys Val Lys Gly Pro Met Leu Met
385                 390                 395                 400

Lys Gly Tyr Val Asn Asn Pro Glu Ala Thr Lys Glu Leu Ile Asp Glu
            405                 410                 415

Glu Gly Trp Leu His Thr Gly Asp Ile Gly Tyr Tyr Asp Glu Glu Lys
        420                 425                 430

His Phe Phe Ile Val Asp Arg Leu Lys Ser Leu Ile Lys Tyr Lys Gly
    435                 440                 445

Tyr Gln Val Pro Pro Ala Glu Leu Glu Ser Val Leu Leu Gln His Pro
    450                 455                 460

Ser Ile Phe Asp Ala Gly Val Ala Gly Val Pro Asp Pro Val Ala Gly
465                 470                 475                 480

Glu Leu Pro Gly Ala Val Val Val Leu Glu Ser Gly Lys Asn Met Thr
            485                 490                 495

Glu Lys Glu Val Met Asp Tyr Val Ala Ser Gln Val Ser Asn Ala Lys
        500                 505                 510

Arg Leu Arg Gly Gly Val Arg Phe Val Asp Glu Val Pro Lys Gly Leu
    515                 520                 525

Thr Gly Lys Ile Asp Gly Arg Ala Ile Arg Glu Ile Leu Lys Lys Pro
    530                 535                 540

Val Ala Lys Met
545

<210> SEQ ID NO 5
<211> LENGTH: 16
<212> TYPE: DNA
<213> ORGANISM: Luciola cruciata

<400> SEQUENCE: 5
accattgtta tactag                                                         16

<210> SEQ ID NO 6
<211> LENGTH: 16
<212> TYPE: DNA
<213> ORGANISM: Luciola cruciata

<400> SEQUENCE: 6
accatcgtga tcctgg                                                         16

<210> SEQ ID NO 7
<211> LENGTH: 16
<212> TYPE: DNA
<213> ORGANISM: Luciola cruciata

<400> SEQUENCE: 7
```

```
gatttgtcaa atttag                                               16

<210> SEQ ID NO 8
<211> LENGTH: 16
<212> TYPE: DNA
<213> ORGANISM: Luciola cruciata

<400> SEQUENCE: 8
gacctgagca acctgg                                               16

<210> SEQ ID NO 9
<211> LENGTH: 16
<212> TYPE: DNA
<213> ORGANISM: Luciola cruciata

<400> SEQUENCE: 9
gtcaaattta gttgag                                               16

<210> SEQ ID NO 10
<211> LENGTH: 16
<212> TYPE: DNA
<213> ORGANISM: Luciola cruciata

<400> SEQUENCE: 10
gagcaacctg gtggag                                               16

<210> SEQ ID NO 11
<211> LENGTH: 16
<212> TYPE: DNA
<213> ORGANISM: Luciola cruciata

<400> SEQUENCE: 11
attgcatctg gcggag                                               16

<210> SEQ ID NO 12
<211> LENGTH: 16
<212> TYPE: DNA
<213> ORGANISM: Luciola cruciata

<400> SEQUENCE: 12
atcgccagcg gcggag                                               16

<210> SEQ ID NO 13
<211> LENGTH: 16
<212> TYPE: DNA
<213> ORGANISM: Luciola cruciata

<400> SEQUENCE: 13
ctttaggtcc taacag                                               16

<210> SEQ ID NO 14
<211> LENGTH: 15
<212> TYPE: DNA
<213> ORGANISM: Luciola cruciata

<400> SEQUENCE: 14
gccatcatca tcacc                                                15

<210> SEQ ID NO 15
<211> LENGTH: 16
<212> TYPE: DNA
<213> ORGANISM: Luciola cruciata
```

```
<400> SEQUENCE: 15
cctaacagac gtggag                                              16

<210> SEQ ID NO 16
<211> LENGTH: 16
<212> TYPE: DNA
<213> ORGANISM: Luciola cruciata

<400> SEQUENCE: 16
atcacccccg agggcg                                              16

<210> SEQ ID NO 17
<211> LENGTH: 16
<212> TYPE: DNA
<213> ORGANISM: Luciola cruciata

<400> SEQUENCE: 17
aacagacgtg gagaag                                              16

<210> SEQ ID NO 18
<211> LENGTH: 16
<212> TYPE: DNA
<213> ORGANISM: Luciola cruciata

<400> SEQUENCE: 18
aacagacggg gcgaag                                              16

<210> SEQ ID NO 19
<211> LENGTH: 16
<212> TYPE: DNA
<213> ORGANISM: Luciola cruciata

<400> SEQUENCE: 19
gaagtttgtg ttaaag                                              16

<210> SEQ ID NO 20
<211> LENGTH: 16
<212> TYPE: DNA
<213> ORGANISM: Luciola cruciata

<400> SEQUENCE: 20
cgacgacaag cctgga                                              16

<210> SEQ ID NO 21
<211> LENGTH: 10
<212> TYPE: DNA
<213> ORGANISM: Luciola cruciata

<400> SEQUENCE: 21
aaactgtgaa                                                     10

<210> SEQ ID NO 22
<211> LENGTH: 10
<212> TYPE: DNA
<213> ORGANISM: Luciola cruciata

<400> SEQUENCE: 22
ttcacagttt                                                     10

<210> SEQ ID NO 23
<211> LENGTH: 10
<212> TYPE: DNA
<213> ORGANISM: Luciola cruciata
```

```
<400> SEQUENCE: 23
gaactgcgag                                                                  10

<210> SEQ ID NO 24
<211> LENGTH: 10
<212> TYPE: DNA
<213> ORGANISM: Luciola cruciata

<400> SEQUENCE: 24
tgcacagcct                                                                  10
```

MODIFIED *LUCIOLA CRUCIATA* LUCIFERASE GENE AND PROTEIN

FIELD OF THE INVENTION

The present invention relates to a novel codon optimized and stabilized luciferase gene (COS luciferase) derived from Japanese firefly *Luciola cruciata* luciferase. The invention further relates to production of a stabilized luciferase protein using such a modified gene.

BACKGROUND OF THE INVENTION

Bioluminescence in certain organisms via the reaction of luciferin and luciferase is well known in the art. The use of the luciferase enzyme has become highly valuable as a genetic marker gene due to the convenience, sensitivity and linear range of the luminescence assay. Luciferase has been used in many experimental biological systems in both prokaryotic and eukaryotic cell culture, transgenic plants and animals, as well as cell-free expression systems.

For example, Japanese Firefly *Luciola cruciata* luciferase expression can be monitored as a genetic marker in cell extracts when mixed with substrates (D-luciferin, $Mg^{2+}$ ATP, and $O_2$), and the resulting luminescence measured using a luminescent detection device (containing a photomultiplier system or equivalent) such as luminometers or scintillation counters without the need of a reagent injection device. The *Luciola cruciata* luciferase activity can also be detected in living cells by adding D-luciferin or more membrane permeant analogs such as D-luciferin ethyl ester to the growth medium. This in vivo luminescence relies on the ability of D-luciferin or more membrane permeant analogs to diffuse through cellular and intracellular organelle membranes and on the intracellular availability of ATP and $O_2$ in these cells.

Despite its utility as a reporter, current luciferases isolated from various organisms, including insects and marine organisms are not necessarily optimized for expression or production in systems that are of most interest to the medical community and experimental molecular biologists. Accordingly, a need exists for a luciferase nucleic acid molecule that allows improved protein production in mammalian cells and tissues.

SUMMARY OF THE INVENTION

The present invention describes a novel codon optimized and stabilized luciferase gene coding for an improved luciferase protein. This new luciferase exhibits long-wavelength light emission, as well as improved thermostability and higher expression levels in mammalian cell systems, compared to native luciferase. Also described is a method of producing a stabilized luciferase protein by inserting a nucleic acid molecule of the present invention into an appropriate microorganism via a vector and culturing the microorganism to produce the stabilized luciferase protein.

BRIEF DESCRIPTION OF THE DRAWINGS

FIG. 1 shows a cleavage map of recombinant plasmid pDC57 DNA with endonuclease restriction enzymes.

FIG. 2 shows a cleavage map of recombinant plasmid pDC99 DNA with endonuclease restriction enzymes.

FIG. 3 shows a comparison of the native *L. cruciata* luciferase sequence with the codon optimized nucleotide sequence of the present invention.

FIG. 4. shows a comparison of Luciferase Expression Levels using the pDC99 vector of the present invention with the *Photinus pyralis* luciferase vector pSV40-GL3 in mammalian cells.

FIG. 5 shows a comparison of the thermal stability of the modified *Luciola cruciata* luciferase protein of the present invention with that of the *Photinus pyralis* wild type protein.

DETAILED DESCRIPTION OF THE INVENTION

The wild-type sequence is known for the luciferase molecule from many different species and numerous modifications to those sequences have been described in the art. The present invention describes modifications to the nucleic acid molecule encoding luciferase in the Japanese firefly, *Luciola cruciata* as well as the luciferase protein itself. In a particular embodiment of the invention, the modified *Luciola cruciata* luciferase nucleic acid molecule encodes an improved luciferase enzyme which demonstrates greater thermostability (see FIG. 5 for an analysis of the thermal stability of the codon-optimized and stabilized *Luciola cruciata* luciferase protein of the present invention versus wild type protein at various temperatures) as well as a wavelength shift from blue to red compared to native luciferase.

In another embodiment of the present invention, mRNA transcribed from the modified luciferase nucleic acid molecule is more stable in mammalian cells. This leads to enhanced levels of mRNA and results in greater expression of the luciferase (see FIG. 4 for a comparison of expression levels using the pDC99 vector of the present invention with the *Photinus pyralis* luciferase vector pSV40-GL3 in mammalian cells). In another embodiment, the level of mRNA is preferably increased by 10% to 200% over that seen when native sequence is expressed in mammalian cells.

In a particular embodiment of the present invention, the modified *Luciola cruciata* luciferase nucleic acid molecule is altered to remove RNAse cleavage motifs. The wild-type sequence shown in SEQ ID NO:1 has RNAse cleavage motifs at nucleotides 384-388, 682-686, and 929-933. In a preferred embodiment, the modified sequence is changed as shown in SEQ ID NO:3 and FIG. 3 to remove these motifs. In particular, nucleotides 384 to 388 are changed from (ATTTA) to GTTCA, nucleotides 682 to 686 are changed from (ATTTA) to ATCTA and nucleotides 929 to 933 are changed from ATTTA) to ACCTG.

Vectors such as retroviral vectors or other vectors intended for the introduction of recombinant DNA into mammalian cells will often contain active splice donor sequences. Instability is often created when a wild type gene from a non-mammal is carried by a retroviral vector due to the recognition of cryptic splice acceptor sequences in the wild type gene and splicing between these and splice donor sites present in the vector. In a particular embodiment of the present invention, cryptic splice acceptor sequences present in the wild type *L. cruciata* luciferase nucleic acid molecule are altered or removed.

In another particular embodiment of the present invention, cryptic splice acceptor sites found at bases 448 to 463, 919 to 934, 924 to 939, 940 to 955, 1148 to 1163, 1156 to 1171, 1159 to 1174, and 1171 to 1186 of the wild type sequence of SEQ ID NO:1 have one or more nucleotides altered.

In a particular embodiment, bases 448 to 463 of the wild type *L. cruciata* luciferase, i.e. ACCATTGTTATACTAG, herein SEQ ID NO:5 are changed in the COS luciferase to ACCATCGTGATCCTGG herein SEQ ID NO:6.

In another embodiment, bases 919 to 934 of the wild type *L. cruciata* luciferase, i.e. GATTTGTCAAATTTAG herein SEQ ID NO:7 are changed in the COS luciferase to GACCT-GAGCAACCTGG herein SEQ ID NO:8.

In another embodiment, bases 924 to 939 of the wild type *L. cruciata* luciferase, i.e. GTCAAATTTAGTTGAG herein SEQ ID NO:9 are changed in the COS luciferase to GAG-CAACCTGGTGGAG herein SEQ ID NO:10.

In another embodiment, bases 940 to 955 of the wild type *L. cruciata* luciferase, i.e. ATTGCATCTGGCGGAG herein SEQ ID NO:11 are changed in the COS luciferase to ATCGC-CAGCGGCGGAG herein SEQ ID NO:12.

In another embodiment, bases 1148 to 1163 of the wild type *L. cruciata* luciferase, i.e. CTTTAGGTCCTAACAG herein SEQ ID NO:13 are changed in the COS luciferase to GCCATCATCATCACC herein SEQ ID NO:14.

In another embodiment, bases 1156 to 1171 of the wild type *L. cruciata* luciferase, i.e. CCTAACAGACGTGGAG herein SEQ ID NO:15 are changed in the COS luciferase to ATCACCCCCGAGGGCG herein SEQ ID NO:16.

In another embodiment, bases 1159 to 1174 of the wild type *L. cruciata* luciferase, i.e. AACAGACGTGGAGAAG herein SEQ ID NO:17 are changed in the COS luciferase to AACAGACGGGGCGAAG herein SEQ ID NO:18.

In another embodiment, bases 1171 to 1186 of the wild type *L. cruciata* luciferase, i.e. GAAGTTTGTGTTAAAG herein SEQ ID NO:19 are changed in the COS luciferase to CGACGACAAGCCTGGA herein SEQ ID NO:20.

In a particular embodiment, the corresponding branchpoint sequences for the above cryptic splice sites in the wild type *L. cruciata* luciferase SEQ ID NO:1, are also altered to further suppress the splicing potential.

Palindromic sequences tend to have an adverse effect on translational efficiency and/or mRNA stability. The degree of these effects are generally directly related to the stability of the loop structures formed by these palindromic motifs. Accordingly, one embodiment of the present invention includes reducing the number of palindromic motifs. In a particular embodiment, palindromic motifs are altered by one or more nucleotides without altering the encoded luciferase enzyme activity and preferably without altering the amino acid sequence.

In a particular embodiment, a palindromic pair of motifs at bases 1087 to 1095 and 1218 to 1226 of the wild type *L. cruciata* luciferase, ie. GCTTCTGGA and TCCAGAAGC, respectively are changed in the COS luciferase to GCCAGCGGC and CCCCGAGGC, respectively.

In a particular embodiment, a palindromic pair of motifs at bases 1151 to 1158 and 1185 to 1192 of the wild type *L. cruciata* luciferase, ie. TAGGTCCT and AGGACCTA, respectively are changed in the COS luciferase to TGGGCCCC and GGGCCCCA, respectively.

In a particular embodiment, a palindromic pair of motifs at bases 255 to 264 and 350 to 359 of the wild type *L. cruciata* luciferase, ie. AAACTGTGAA and TTCACAGTTT, herein SEQ ID NO: 21 and SEQ ID NO:22 respectively are changed in the COS luciferase to GAACTGCGAG and TGCACAGCCT herein SEQ ID NO:23 and SEQ ID NO:24, respectively.

In a particular embodiment, a palindromic pair of motifs at bases 1381 to 1389 and 1508 to 1516 of the wild type *L. cruciata* luciferase, ie. TTGCAACAT and ATGTTGCAA, respectively are changed in the COS luciferase to CTGCAGCAC and ACGTCGCCA, respectively.

In a particular embodiment, a palindromic pair of motifs at bases 235 to 242 and 883 to 890 of the wild type *L. cruciata* luciferase, ie. AGAATTGC and GCAATTCT, respectively are changed in the COS luciferase to CGGATCGC and GCCATCCT, respectively.

In a particular embodiment, a palindromic pair of motifs at bases 445 to 452 and 740 to 747 of the wild type *L. cruciata* luciferase, ie. AAAACCAT and ATGGTTTT, respectively are changed in the COS luciferase to AAGACCAT and ACGGCTTC herein SEQ ID NO:43, respectively.

The wild type *Luciola cruciata* sequence incorporates several negatively cis-acting motifs that hamper expression in mammals are found in the wild-type sequence. In a particular embodiment of the present invention, the modified sequence contains no negative cis-acting sites (such as splice sites, poly(A) signals, etc.) which would negatively influence expression in mammalian cells.

The wild type *Luciola cruciata* sequence has a GC content that is quite low compared to mammalian sequences, which facilitates quick mRNA turnover. In another embodiment, the GC-content of the modified luciferase sequence is increased from about 37% to about 62%, prolonging mRNA half-life. Codon usage was adapted to the bias of *Homo sapiens* resulting in a high CAI (codon adaptation index) value of 0.97, in comparison to 0.62 for the wild-type sequence. Accordingly, the optimized gene provides high and stable expression rates in *Homo sapiens* or other mammalian cell types.

The codon usage alterations generally lead to an increase the translation efficiency of the messenger RNA in a mammalian cell. It is a feature of the present invention that mRNA transcribed from the modified luciferase gene is more stably present in mammalian cells. This leads to enhanced levels of mRNA and results in greater expression of the luciferase protein. In a particular embodiment of the present invention, the level of mRNA is increased by 10% to 200% compared to expression of the native gene in the same cell. The codon optimization modifications are preferably incorporated such that resulting modified enzyme activity is not altered and most preferably that the amino acid sequence is not altered, except for desired changes described herein.

Many organisms display a bias for use of particular codons to code for addition of a specific amino acid in a growing peptide chain. Codon biases for differences in codon usage between organisms often correlate with the efficiency of translation of messenger RNA (mRNA), which in turn is believed to result from the properties of the codons being translated and the availability of particular transfer RNA (tRNA) molecules to be used in translation of the mRNA into protein. The predominance of selected tRNAs in a cell is generally a reflection of the codons used most frequently in peptide synthesis.

Codon usage in highly expressed mammalian genes are as follows:

[AminoAcid Codon Fraction] Gly GGG 0.15 Gly GGA 0.18 Gly GGT 0.21 Gly GGC 0.46 Glu GAG 0.68 Glu GAA 0.32 Asp GAT 0.38 Asp GAC 0.62 Val GTG 0.54 Val GTA 0.08 Val GTT 0.14 Val GTC 0.25 Ala GCG 0.14 Ala GCA 0.13 Ala GCT 0.29 Ala GCC 0.44 Arg AGG 0.14 Arg AGA 0.13 Ser AGT 0.10 Ser AGC 0.25 Lys AAG 0.75 Lys AAA 0.25 Asn AAT 0.26 Asn AAC 0.74 Met ATG 1.00 Ile ATA 0.06 Ile ATT 0.26 Ile ATC 0.67 Thr ACG 0.09 Thr ACA 0.18 Thr ACT 0.23 Thr ACC 0.50 Trp TGG 1.00 End TGA 0.30 Cys TGT 0.46 Cys TGC 0.54 End TAG 0.16 End TAA 0.53 Tyr TAT 0.35 Tyr TAC 0.65 Leu TTG 0.10 Leu TTA 0.03 Phe TTT 0.35 Phe TTC 0.65 Ser TCG 0.07 Ser TCA 0.08 Ser TCT 0.20 Ser TCC 0.31 Arg CGG 0.11 Arg CGA 0.05 Arg CGT 0.17 Arg CGC 0.40 Gln CAG 0.82 Gln CAA 0.18 His CAT 0.35 His CAC 0.65 Leu CTG 0.56 Leu CTA 0.05 Leu CTT 0.08 Leu CTC 0.18 Pro CCG 0.16 Pro CCA 0.19 Pro CCT 0.30 Pro CCC 0.35 The codon bias in the Gene is different to the highly expressed mammalian genes. Of the codons that potentially encode a particular amino some are very rarely used.

By the standard set forth in the preceding paragraph, the wild type *Luciola cruciata* sequence uses codons rarely used in mammalian systems with a high frequency. To have the most impact the most rarely used codons in highly expressed mammalian genes are preferably changed. In one embodiment of the present invention, at least about 90% of the rarely used codons found in the wild type sequence are altered to more preferred codons for the corresponding amino acid.

For example, the codon TTA is used to encode leucine in only 3% of cases in highly expressed mammalian systems, but is seen in the wild type luciferase of SEQ ID NO:1 at positions 87-89, 246-248, 339-341, 360-362, 405-407, 720-722, 774-776, 801-803, 828-830, 906-908, 933-935, 963-965, 1032-1034, 1152-1154, 1329-1331, 1368-1370, and 1542-1544. In one embodiment of the present invention, each of these positions is changed to CTG, which is a more commonly used in mammalian systems, thus optimizing the nucleic acid sequence for expression in mammals without changing the amino acid sequence. A preferred altered *Luciola cruciata* Luciferase gene is one where at least about 70%, 80%, 90%, 95%, 99% or 100% of codons are thus optimized for expression in a particular cell system. A specific embodiment of the present invention is the codon optimized and stabilized (COS) Luciferase set forth in SEQ ID NO:3

In another embodiment of the present invention, it is anticipated that conservative amino acid substitutions might be made throughout the enzyme without adversely altering the enzyme activity. One or more amino acid residues within the sequence can be substituted by another amino acid of a similar polarity, which acts as a functional equivalent, resulting in a silent alteration.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Particularly conservative amino acid substitutions are: (a) Lys for Arg or vice versa such that a positive charge may be maintained; (b) Glu for Asp or vice versa such that a negative charge may be maintained; (c) Ser for Thr or vice versa such that a free OH can be maintained; (d) Gln for Asn or vice versa such that a free $NH_2$ can be maintained; (e) Ile for Leu or for Val or vice versa as roughly equivalent hydrophobic amino acids; and (0 Phe for Tyr or vice versa as roughly equivalent aromatic amino acids. However it will be understood that less conservative substitutions may still be made without affecting the activity of the resulting luciferase enzyme.

In a particular embodiment of the present invention, the amino acid encoded at nucleotide position 875-877 in the wild-type sequence, SEQ ID NO:1 is changed from Ser(S) to Tyr(Y). This nucleic position corresponds with position 286 of the wild-type protein sequence, SEQ ID NO:2. This modification was found to have the surprising effect of making the resulting protein >100-fold more stable after 1 hour and >1000-fold more stable after 2 hours at 37° C. The modified luciferase also demonstrated greater thermostability than wild-type protein at room temperature. The substitution of Tyr for Ser at this position was also shown to have the surprising effect of shifting the emitted light from blue to red (from 582 nm to 619 nm (pH 6)).

The present invention also anticipates similar conservative amino acid substitutions at nucleotide position 875-877, including substituting Tyr, Lys, Leu, or Gln for Ser.

It will be understood that the invention also encompasses a method of using the modified luciferase gene as a marker gene in live cells, wherein the nucleic acid molecules encoding the modified luciferase gene are provided in an expression vector with appropriate cis- and trans-acting expression elements and thereby provide cells expressing the modified luciferase gene that produce the modified enzyme intracellularly.

The modified luciferase of the present invention might be incorporated as part of a fusion protein. Additionally the invention encompasses a cloning vehicle having a sequence encoding the modified luciferase gene.

The luciferase gene will typically be positioned operably linked to a promoter. Preferably the promoter is a mammalian promoter, and may be selected from one of the many known mammalian promoters. In the context of this invention the term luciferase gene refers to the open reading frame encoding the modified luciferase protein.

Additionally other nucleotide motifs might be introduced to enhance transcription and/or translation such as a Kozak consensus sequence or transcriptional enhancers.

The present invention describes a plasmid vector for expression in mammalian cells, a bacterial vector for expression in plant cells, but also contemplates a retroviral vector or a lentiviral vector, that includes the modified luciferase gene, or a cell carrying the modified luciferase gene.

The examples below are given so as to illustrate the practice of this invention. They are not intended to limit or define the entire scope of this invention.

EXAMPLES

Example 1

Construction of the Modified *Luciola cruciata* Luciferase Gene

The synthetic COS luciferase gene, SEQ ID NO:3, was assembled from synthetic oligonucleotides and/or PCR products. The fragment was cloned into pMK (kanR) using KpnI and SacI restriction sites. The plasmid DNA was purified (PureYield™ Plasmid Midiprep, Promega) from transformed bacteria and concentration determined by UV spectroscopy. The final construct was verified by sequencing. The sequence congruence within the used restriction sites was 100%.

Example 2

Subcloning of the Modified *Luciola cruciata* Luciferase Gene into the pCMV and pSV40 Vectors The synthetic COS luciferase assembled in Example 1 was excised from pMK cloning vector using flanking XhoI and NotI restriction enzymes (Fast Digest, Fermentas). The excised fragment was gel-purified (GenElute Gel Extraction Kit, Sigma) and quantitated using MassRuler™ DNA Ladder Mix (Fermentas). The excised gene was subcloned into both pCMV and pSV40 Mammalian Expression Vectors using corresponding XhoI and NotI restriction sites. The completed pCMV construct was named pDC57. The completed pSV40 construct was named pDC99.

Example 3

Subcloning of the Modified *Luciola cruciata* Luciferase Gene into the pNosdc Binary Vector for Expression in Plants The synthetic COS luciferase assembled in Example 1 was amplified using the Polymerase Chain reaction. Amplification was performed with primers including XmaI and SacI restriction sites. The ends of the amplified fragment were cut with XmaI and SacI restriction enzymes (New England Biolabs) and the fragment was gel-purified (GenElute Gel Extraction Kit, Sigma) and quantitated using MassRuler™ DNA Ladder Mix (Fermentas). The amplified fragment was subcloned into the pNosdc binary vector for transformation of plants via *Agrobacterium tumefaciens*. The completed construct was named pNosdcCOS.

Example 4

Transfection of Mammalian Cells with the Modified *Luciola cruciata* Luciferase Vectors pDC57 and pDC99

NIH 3T3 cells (murine tumor fibroblasts) were grown to 80% confluence in 100 mm tissue culture plates. Cells were transfected with either pDC57 or pDC99 using Lipofectamine and PLUS reagents (Invitrogen).

Example 5

Analysis of Luciferase Expression Levels Using the pDC99 Vector and Comparison to the Luciferase Expression Using the *Photinus pyralis* Luciferase Vector pSV40-GL3 in Mammalian Cells Transfected NIH 3T3 cells prepared in Example 4 were lysed using a lysis buffer comprised of 25 mM Tris-phosphate (pH 7.8), containing 10% glycerol, 1% Triton X-100, 1 mg/ml BSA, 2 mM EGTA and 2 mM DTT. Cells were washed with 1× Phosphate Buffered Saline, and lysis buffer (1 mL) was added to surface of plate. Plate was incubated for 30 mins, and lysate was collected. Additionally, NIH 3T3 cells were transfected with pSV40-GL3, a construct containing wild type luciferase from *Photinus pyralis*, as per the method in Example 4 and lysed using the above method. As a negative control, untransfected NIH 3T3 cells were also lysed by the above method.

Cell lysates were diluted using lysis buffer, and added in triplicate to wells of a solid white 96-well plate (Costar). Added to cell lysates was a reagent containing 1 mM D-luciferin and 2 mM, ATP in a buffer comprised of 25 mM Glycylglycine, 15 mM MgSO4, 4 mM EDTA, 15 mM Potassium phosphate pH 7.8, 1 mM DTT, and 1 mM Coenzyme A.

Luminescence was recorded using a Perkin-Elmer HTS7000 Plus Bio Assay Reader (200 ms integration time). Results of these analyses are shown in FIG. 4.

Example 6

Analysis of the Thermal Stability of the Modified *Luciola cruciata* Luciferase Protein Versus Wild Type Protein Cell lysates from NIH 3T3 cells transfected with pDC99 and pSV40-GL3 (transfected according to method in Example 4), as well as untransfected cells were prepared as described in Example 5a. Luminescence of each sample was recorded as described in Example 5a to obtain a baseline value of enzyme activity. Portions of each sample were then incubated in water baths at 37° C., 42° C., and 55° C. A portion of each sample was also incubated at ambient room temperature (25° C.). At 1 hour and 2 hour intervals, aliquots of each temperature-incubation were removed and assayed for activity using the method described in Example 5a. Results of these analyses are shown in FIG. 5.

Example 7

Isolation of the Modified *Luciola cruciata* Luciferase Protein from Bacterial Culture

*Escherichia coli* (strain JM109) harboring a plasmid vector containing a Histidine tag (such as pDEST17 (Invitrogen), pET-14b (Novagen and pQE (Qiagen)) fused to the codon optimized and stabilized luciferase gene (COS) are grown to an OD600 of 0.2 by incubation at 37° C. with vigorous shaking in 250 mL LB Broth containing the appropriate selection antibiotic. Bacterial cells are pelleted by centrifugation at 5,000×g, and the pellet is resuspended in a bacterial cell lysis buffer, such as CellLytic B (Sigma Prod. No. B7435). The suspension is incubated for 15 mins to extract soluble proteins, and then centrifuged at >15,000×g for 10 mins to pellet insoluble debris. The lysate is applied to an affinity column (such as HIS-Select, Sigma Prod. No. H7787) equilibrated with 0.1M sodium phosphate, 8M urea, pH 8.0 (equilibration buffer). Impurities are removed by washing the column several times with equilibration buffer. The His-tagged COS protein is eluted from the column using an acidic buffer, such as 0.1 M sodium phosphate, 8 M urea, with a pH in the 4.5-6.0 range. The eluate contains the recombinant codon optimized and stabilized luciferase protein. The purified protein is then dialyzed against H2O and lyophilized. The lyophilized protein is dissolved in reaction buffer (25 mM Glycylglycine, 15 mM MgSO4, 4 mM EDTA, 15 mM Potassium phosphate pH 7.8, 1 mM DTT, and 1 mM Coenzyme A) or dH$_2$O and assayed by adding a reagent containing 1 mM D-luciferin and 2 mM ATP in reaction buffer.

Luminescence is recorded using a Perkin-Elmer HTS7000 Plus Bio Assay Reader (200 ms integration time).

Example 8

Transfection of Plants with Codon Optimized and Stabilized Luciferase

COS

*Agrobacterium tumefaciens* are transfected with pdc-NosCOS according to freeze-thaw protocol previously described (D. Weigel, J. Glazerbrook, pp. 125-126 (2002)). *Arabidopsis thaliana* (strain CS-20) are transfected by the floral dip method using the aforementioned transfected *Agrobacterium*, using the protocol described previously (D. Weigel, J. Glazerbrook, pp. 129-130 (2002)). Seedlings are selected on Murashige and Skoog Agar plates containing 50 μg/mL kanamycin, as described previously (D. Weigel, J. Glazerbrook, pp. 131-132 (2002)).

Protein is extracted from plant tissue according to the following procedure: Tissue is lyophilized and ground into a fine powder in a mortar. The powder is placed in a microcentrifuge tube and suspended in reaction buffer (25 mM Glycylglycine, 15 mM MgSO4, 4 mM EDTA, 15 mM Potassium phosphate pH 7.8, 1 mM DTT, and 1 mM Coenzyme A) by vortexing. The tube is incubated at 10 mins at room temperature to solubilize proteins, followed by centrifugation at >15,000×g to pellet solid material. The supernatant is transferred to a fresh tube, and added in triplicate to wells of a solid white 96-well plate (Costar). Added to tissue extracts is a reagent containing 1 mM D-luciferin and 2 mM ATP in a buffer comprised of 25 mM Glycylglycine, 15 mM MgSO4, 4 mM EDTA, 15 mM Potassium phosphate pH 7.8, 1 mM DTT, and 1 mM Coenzyme A.

Luminescence is recorded using a Perkin-Elmer HTS7000 Plus Bio Assay Reader (200 ms integration time).

It is to be understood that, while the foregoing invention has been described in detail by way of illustration and example, numerous modifications, substitutions, and alterations are possible without departing from the spirit and scope of the invention as described in the following claims.

What is claimed is:

1. An isolated nucleic acid molecule comprising the nucleic acid sequence as set forth in SEQ ID NO:3.

2. The isolated nucleic acid molecule of claim 1, wherein said molecule encodes a protein comprising SEQ ID NO:4.

3. A plasmid comprising the isolated nucleic acid molecule of claim 1.

4. The plasmid of claim 3, wherein said plasmid contains one or more regulatory elements allowing expression in mammalian, bacterial or plant cells.

5. The plasmid of claim 3, wherein said plasmid is selected from the group consisting of pCMV and pSV40.

6. A method of producing a luciferase protein encoded by the nucleic acid molecule of claim 1, said method comprising: culturing, in a medium, a microorganism belonging to the genus *Escherichia* having inserted therein the nucleic acid of claim 1 and collecting the luciferase protein from the culture.

7. A method for producing the luciferase protein according to claim 6, wherein said nucleic acid molecule is inserted into a plasmid DNA vector containing a Histidine tag and expressed in bacterial cells.

* * * * *